United States Patent [19]

Sano et al.

[11] 4,383,906

[45] May 17, 1983

[54] DEVICE FOR SENSING OXYGEN CONCENTRATION IN AN EXHAUST GAS

[75] Inventors: Hiromi Sano, Nagoya; Masatoshi Suzuki, Anjo, both of Japan

[73] Assignee: Nippondenso Co., Ltd., Kariya, Japan

[21] Appl. No.: 401,027

[22] Filed: Jul. 22, 1982

[30] Foreign Application Priority Data

Jul. 27, 1981 [JP] Japan .............................. 56-117406

[51] Int. Cl.$^3$ ............................................ G01N 27/46
[52] U.S. Cl. .................................. 204/416; 204/1 T; 204/424; 204/432
[58] Field of Search ................. 204/195 S, 195 R, 1 T

[56] References Cited

U.S. PATENT DOCUMENTS

| | | | |
|---|---|---|---|
| 4,141,813 | 2/1979 | Kita et al. | 204/195 S |
| 4,145,272 | 3/1979 | Nakamura | 204/195 S |
| 4,157,948 | 6/1979 | Maurer | 204/195 S |
| 4,189,355 | 2/1980 | Fujishiro | 204/195 S |
| 4,227,984 | 10/1980 | Dempsey et al. | 204/195 S |
| 4,265,714 | 5/1981 | Nolan et al. | 204/195 S |
| 4,302,312 | 11/1981 | Ishitani et al. | 204/195 S |

*Primary Examiner*—Arthur P. Demers
*Attorney, Agent, or Firm*—Cushman, Darby & Cushman

[57] ABSTRACT

A device for sensing the oxygen concentration in an exhaust gas has a cup-like oxygen-ion permeable cylindrical member made of solid electrolyte consisting of oxygen-ion conducting metal oxide. The cylindrical member has an inner circumferential surface communicating with the atmosphere and an outer circumferential surface communicating with the exhaust gas for producing an electromotive force corresponding to a difference between the oxygen concentrations on the inner circumferential surface and on the outer circumferential surface and has a negative-resistance temperature characteristic. A pair of first electrodes serving as a lean sensor each comprise a thin film made of porous metal material and are provided on the inner circumferential surface and outer circumferential surface of the cylindrical member, respectively, in opposed relationship to each other. An oxygen-gas diffusion limiting layer covers the lean sensing electrode on the outer circumferential surface of the cylindrical member. A pair of second electrodes for sensing the oxygen concentration under high load drive mode and the temperature of the cylindrical member each comprises a thin film made of porous metal material and are provided, respectively, on those portions of the inner and outer circumferential surfaces of the cylindrical member which are different from the portions where the first electrodes are provided in opposed relationship to each other. A heater is disposed in the cylindrical member for heating the cylindrical member.

10 Claims, 3 Drawing Figures

F I G. 2
F I G. 3
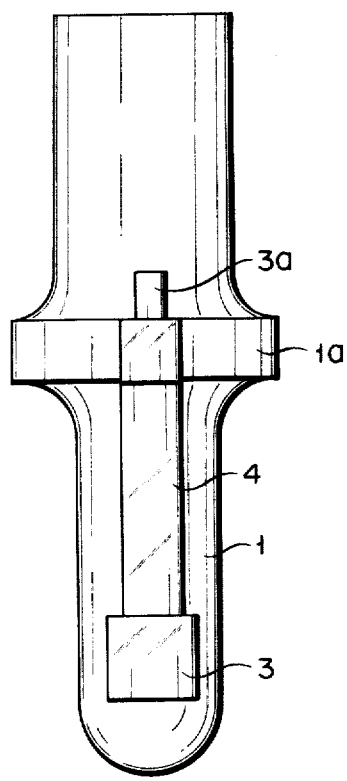
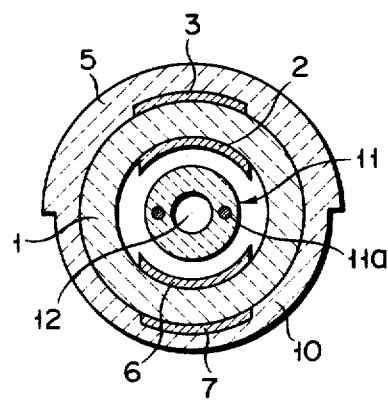

1

DEVICE FOR SENSING OXYGEN CONCENTRATION IN AN EXHAUST GAS

BACKGROUND OF THE INVENTION

This invention relates to a device for sensing the oxygen concentration in an exhaust gas, which is used to control the supply of fuel to an internal combustion engine.

Generally, when an internal combustion engine is being driven at the stoichiometrical air-fuel ratio, the amount of harmful components in the exhaust gas extremely decreases. In order to avoid air contamination, therefore, it is desirable that the internal combustion engine be driven at the stoichiometrical air-fuel ratio under any operation mode. However, this would increase the consumption of fuel. At the time of acceleration drive or high load drive, the air-fuel mixture is made rich, while at the time of normal drive or partial load drive it is made lean. Therefore, if the amount of fuel supplied to the internal combustion engine is so adjusted or controlled that at the time of high load drive, the engine may be driven at the stoichiometrical air-fuel ratio and that when the engine is used a lean mixture condition at the time of partial load drive, the amount of supplied fuel may be adjusted to an ideal one in accordance with the concentration of oxygen residual in the exhaust gas. Thus, the countermeasure against the exhaust gas and the saving of the fuel will be realized.

There has been developed a control means which, when the engine is driven, in at a high-load and a partial-load, senses the amount of oxygen in the exhaust gas and controls the amount of fuel injected from a fuel injecting device in correspondence to the amount of oxygen gas thus sensed. As the elements of this control means, two types of sensors have been developed, one of which is a stoichiometrical air-fuel ratio sensor designed to sense under a high load drive mode whether or not the oxygen concentration in the exhaust gas corresponds to the oxygen concentration of the air-fuel mixture at the stoichiometrical air-fuel ratio, and the other of which is a lean sensor designed to sense the oxygen concentration in the exhaust gas under the partial load drive mode or under lean mixture mode.

The stoichiometrical air-fuel ratio sensor has an oxygen concentration sensing element made of oxygen-ion permeable metal oxide and producing an electromotive force in correspondence to the oxygen concentration in the exhaust gas, said electromotive force being delivered from two electrodes made of, for example, platinum and provided on the sensing element. This electromotive force is suddenly changed when the stoichiometrical air-fuel ratio is attained, the driving mode corresponding to the stoichiometrical air-fuel ratio is achieved by increasing or decreasing the amount of fuel supplied to the engine until said electromotive force indicates such a sudden change.

The lean sensor comprises a solid electrolyte element made of oxygen-ion permeable metal oxide. The element is provided with a pair of porous electrodes on both surfaces. Oxygen in the exhaust gas is ionized by applying a voltage between the electrodes so that the resulting ions are diffused from one electrode to the other.

Generally, when the voltage applied between both electrodes is varied, the amount of current flowing between them is also varied. At the time of an optimum air-fuel ratio under a lean mode, however, if the solid electrolyte element is at a fixed temperature, the amount of current ceases to vary even if the applied voltage is varied. The unvaried current is hereinafter referred to as "a saturated current". Under a lean mode, therefore, an optimum air-fuel ratio is achieved by increasing or decreasing the amount of fuel supplied to the engine until said saturated current flows between the electrodes.

Since the value of the above-mentioned saturated current varies with a temperature, it is necessary to keep the temperature to be a fixed value. To this end, while checking a temperature sensor is used to control a heater so that the solid electrolyte element is kept at a constant temperature within the range of, for example, 700° to 750° C.

When it is attempted, under such circumstances, to control the supply of fuel to the internal combustion engine throughout one entire operation including any type of driving modes, it becomes necessary to use the stoichiometrical air-fuel ratio sensor, the lean sensor, the heater for the lean sensor and the temperature sensor for the heater. In the prior art, however, those sensors are separately prepared, or only the lean and temperature sensors are assembled together. In the prior art, therefore, in controlling the air-fuel ratio throughout the entire operation range of the internal combustion engine it is necessary to connect a plurality of such independent sensors to, for example, the exhaust pipe of the engine. This results in an increase in number of parts as well as in number of the assembling processes. Thus, the prior art has the disadvantages that such factors increases the cost.

SUMMARY OF THE INVENTION

The object of the invention is to provide a device for sensing the oxygen concentration in an exhaust gas which is designed to sense, by means of one unit, both the oxygen concentration in the exhaust gas from an internal combustion engine under the modes of high load drive and partial load drive and the temperature of an oxygen-ion permeable cylindrical member under the mode of partial load drive, thereby to sense the air-fuel ratio of the engine throughout its one entire operation.

According to the invention, there is provided a device for sensing the oxygen concentration in a exhaust gas which comprises a cup-like oxygen-ion permeable blind-ended cylindrical member made of solid electrolyte such as oxygen-ion permeable metal oxide, which has an inner circumferential surface communicating with the atmosphere and an outer circumferential surface communicating with an exhaust gas, which produces an electromotive force corresponding to the difference between the oxygen concentrations on the inner circumferential surface and the outer circumferential surface and which has negative-resistance temperature characteristic, a pair of first electrodes serving as a lean sensor and each comprising a thin film made of porous metal material and provided on the inner circumferential surface and outer circumferential surface of the cylindrical member in opposed relationship to each other, an oxygen-gas diffusion limting layer covering the first electrode on the outer circumferential surfaces of the cylindrical member, a pair of second electrodes for sensing the oxygen concentration of the exhaust gas under high load drive mode and the temperature of the cylindrical member and each comprising a thin film made of porous metal material, said second electrodes being provided on those portions of the inner and outer circumferential surfaces of the cylindrical member which are different from the portions where the first electrodes are provided in opposed relationship to each other, and a heater disposed in the cylindrical member for heating the same.

The present invention is characterized particularly in that the lean sensing, oxygen concentration sensing and temperature sensing are carried out by means of a single unit.

BRIEF DESCRIPTION OF THE DRAWINGS

This invention can be fully understood from the following detailed description with reference to the accompanying drawings in which:

FIG. 2 is a front view of an oxygen ion conducting cylindrical member used in the device shown in FIG. 1; and FIG. 3 is a cross sectional view of the cylindrical member in FIG. 1.

DETAILED DESCRIPTION OF THE PREFERRED EMBODIMENT

Figure 1:
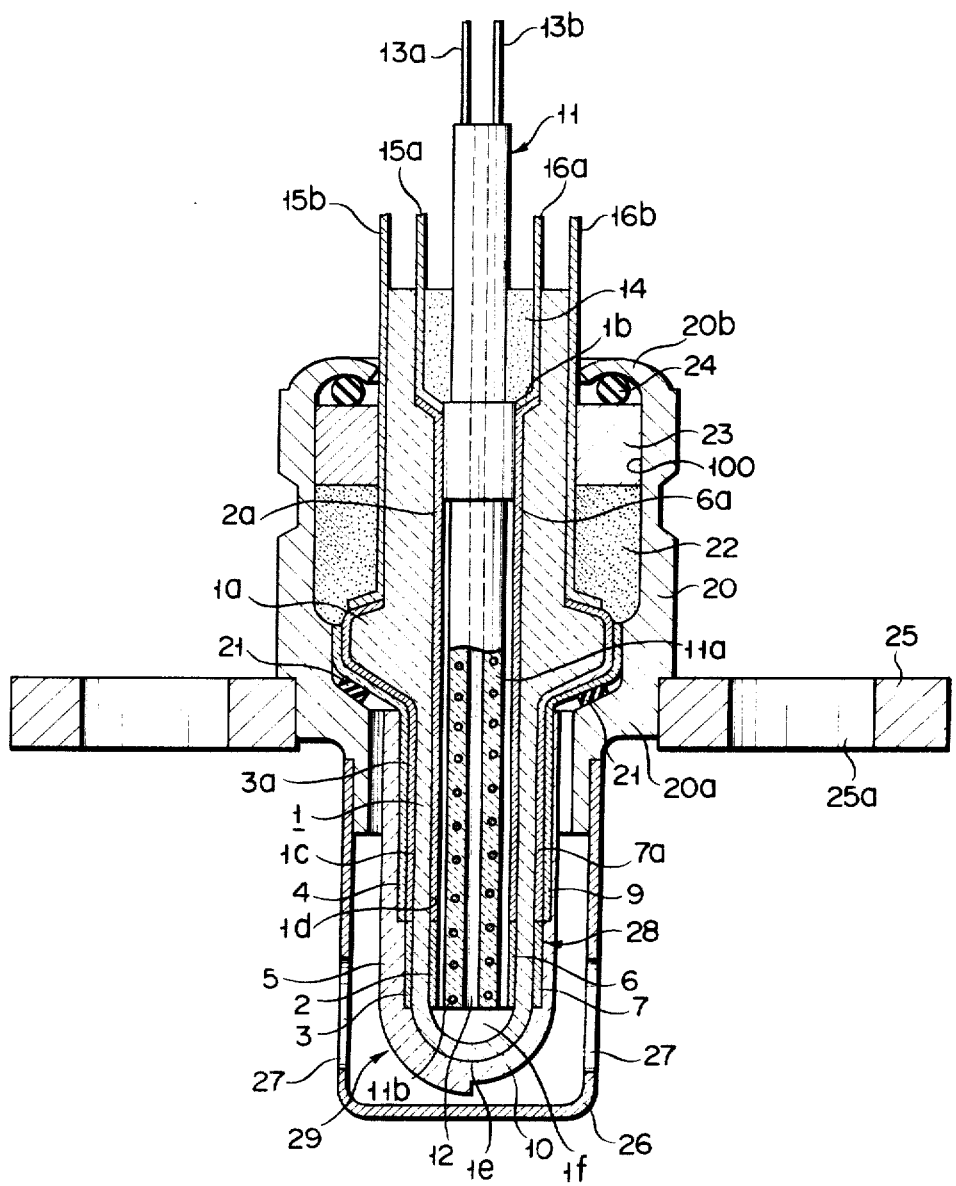
FIG. 1 is a longitudinal sectional view showing a device for sensing the oxygen concentration in an exhaust gas according to an embodiment of this invention.

Referring to FIGS. 1 and 2, an oxygen ion permeable cup like cylindrical member is opened at one end and closed at the other end and has an inner diameter of substantially 5 mm and a wall thickness of approximately 0.6 to 1 mm. The cylindrical member 1 is made of solid electrolyte consisting of oxygen ion permeable metal oxide which produces an electromotive force corresponding to oxygen concentration in an exhaust gas and has negative-resistance temperature characteristic. A typical metal oxide having such three properties is a mixture of 96 to 90 mol% of zirconium oxide and 4 to 10 mol% of yttrium oxide. After ground, the mixture is burnt at a temperature of approximately 1,250° C. and then molded into a cup-like shape. Thereafter it is burnt again at a temperature of 1,350° to 1,750° C. and sintered to form the cylindrical member 1. Other suitable materials are $ZrO_2$-$Yb_2O_3$, $ZrO_2$-$Sc_2O_3$, $ZrO_2$-CaO, $ZrO_2$-$Th_2O_3$, $ZrO_2$-MgO, $ThO_2$-CaO and $CeO_2$-MgO.

The cylindrical member 1 has an annular enlarged portion 1a at its center, and also has an annular seat portion 1b on the inner circumferential surface 1d at its top open end. Fixed to the inner circumferential surface 1d of the cylindrical member 1 is a lean-sensing electrode 2, the lower end of which is disposed 2 to 10 mm above the lower end of the inner circumferential surface 1d (FIGS. 1 and 3). Fixed to the outer circumferential surface 1c of the cylindrical member 1 is another lean-sensing electrode 3 in opposed relationship to the electrode 2 (FIGS. 1 and 3). Each of the electrodes (hereinafter referred to as "first electrodes") 2, 3 comprises a porous material film such as a platinum film which is formed on the cylindrical member 1 by, for example, chemical plating or paste-screen printing. The area and the thickness of the first electrodes 2, 3 are substantially 100 mm$^2$ and 0.5 to 1.0 micrometer, respectively. Connected to the first electrodes 2, 3 are lead wires 2a, 3a made of the same material as that which the first electrodes 2, 3 are made of. The lead wire 2a connected to the inner electrode 2 extends up to the top of the annular seat portion 1b along the inner circumferential surface 1d of the cylindrical member 1. The lead wire 3a connected to the outer electrode 3 extends up to the top surface of the annular enlarged portion 1a along the outer circumferential surface 1c of the cylindrical member 1. The outer lead wire 3a is covered with a protecting layer 4 made of, for example, a borosilicate glass having no gas permeability and a high melting point. The outer electrode 3 is covered with a porous oxygen-gas diffusion limiting layer 5 of $Al_2O_3$, $Al_2O_3$.MgO or $ZrO_2$ by plasma melt-injection. In order to sufficiently perform the oxygen-gas diffusing function as later described, the oxygen-gas diffusion limiting layer 5 is designed to meet the strict requirements to the thickness, porosity, average pore size, or the like.

To that portion of the inner circumferential surface 1d of the cylindrical member 1 which is near the closed end 1e thereof but which is different from the portion where the electrode 2 is provided, there is fixed an electrode 6 serving both as a means to sense the oxygen concentration under the high load drive mode and as a means to sense the temperature of the cylindrical member. To the outer circumferential surface 1c of the cylindrical member 1 there is fixed, in an opposed relationship to the electrode 6, another electrode 7 serving the same purpose as the electrode 6 (FIGS. 1 and 3). Each of the electrodes 6, 7 (hereinafter referred to as "second electrodes") comprises a material layer capable of acting as a catalyst, such as platinum layer, formed on its corresponding circumferential surface of the cylindrical member 1 by, for example, chemical plating, paste-screen printing, and has the area of 10 to 100 mm$^2$ and the thickness of 0.1 to 1.0 micrometer. The second electrodes 6, 7 are connected to lead wires 6a, 7a, respectively which are also made of platinum or similar material. The lead wire 6a of the inner second electrode 6 is led to the top of the annular seat portion 1b along the inner circumferential surface 1d of the cylindrical member 1, while the lead wire 7a of the outer electrode 7 is led to the top surface of the annular enlarged portion 1a along the outer circumferential surface 1c of the cylindrical member 1. The outer surface of the outer lead 7a is covered with a dense protecting layer 9 made of glass having a high melting point such as, for example, a borosilicate glass. Further, the outer second electrode 7 is covered with a porous protecting film 10. The protecting film 10 may be separately made from the oxygen gas diffusion limiting layer 5 but it is convenient to make the film 10 integral with the layer.

First, the porous material is applied by plasma melt-injection onto those portions of the outer circumferential surface 1c of the cylindrical member 1 on which the oxygen gas diffusion limiting layer 5 and the protecting layer 10 are to be formed, so as to have the same thickness (100 micrometers) as that of the protecting layer 10. Then, the porous material is further applied by plasma melt-injection onto only the portion where the oxygen gas diffusion limiting layer 5 is to be formed until it has come to have an additional thickness of 100 to 700 micrometers. Thus, both the layers 5, 10 are integrally formed.

A bar-like ceramic heater 11 comprises a cylindrical main body 11a made of ceramic (for example, alumina) and a coil or comb-like heating wire 11b (for example, nickrome wire) received in the main body 11a. The heater 11 is inserted into a space defined by the inner cylindrical circumferential surface 1d of the cylindrical member 1, and has its lower end fixed by an inorganic adhesive agent 14 onto the inner circumferential surface 1d of the cylindrical member 1 at the open end thereof.

The cylindrical ceramic heater 11 is coaxially formed with a bore 12 through which the interior of the cylindrical member 1 communicates with the atmosphere. Interposed between the inorganic adhesive agent 14 and the cylindrical member 1 are metal lead wires 15a, 16a made of, for example, platinum. The lower end of the lead wire 15a is electrically connected to the upper end of the lead wire 2a for the lean sensor and the upper end thereof is electrically connected to a microcomputer located outside the device for sensing the oxygen concentration. The lower end of the other lead wire 16a is electrically connected to the upper end of lead wire 6a for the electrode 6 or sensor of the oxygen under the high load drive mode and the temperature of the member 1 and the upper end thereof is also electrically connected to the microcomputer.

Lead wires 15b and 16b extends axially on the outer peripheral surface of the cylindrical member 1.

The lower end of the lead wire 15b is electrically connected to the upper end of the lead wire 3a and its upper end is electrically connected to the microcomputer. The lower end of the lead wire 16b is connected to the upper end of the electrode 7 serving both as the stoichiometrical air-fuel ratio sensor or oxygen sensor under the high load drive mode and as the tempereture sensor. The other end of the lead wire 16b is electrically connected to the microcomputer.

A cylindrical housing 20 made of metal surrounds the cylindrical member 1 over the region from the annular enlarged portion 1a to the open end portion and holds the member 1. An annular seat portion 20a is formed at the lower end portion of the housing 20. On the inner surface of the annular seat portion 20a, the underside of the annular enlarged portion 1a of the cylindrical member 1 is located with a frusto-conical packing 21 interposed therebetween. Into a space 100 defined between the inner circumferential surface of the housing 20 and the upper outer circumferential surface of the cylindrical member 1 extending from the annular enlarged portion 1a toward the open end portion of the cylindrical member 1, a talc 22 is first filled in the form of a ring and an asbestos ring 23 is then disposed on the talc 22. Both the talc 22 and the ring 23 are used for electrical insulation and sealing between the cylindrical member 1 and the housing 20.

The housing 20 forms an annular calked portion 20b at the upper end and holds the asbestos ring 23 by the calked portion 20b with an O-ring 24 interposed between the ring 23 and the portion 20b such that the cylindrical member 1 is prevented from slipping off the housing 20.

A mounting frange 25 is, for example, welded to the housing 20. The flange 25 is fixed to the exhaust pipe of an internal combustion engine by means of bolts inserted into holes 25a formed in the flange 25 in such a manner that the closed end of the cylindrical member 1 is disposed in the exhaust gas from the engine.

Fixed to the lower end of the housing 20 there is a cover 26 for covering the lower end portion of the cylindrical member 1, said cover 26 being provided with a plurality of exhaust-gas introducing openings 27.

The second electrodes 6, 7, the lead wires 6a, 7a connected thereto, and the portion of the cylindrical member 1 between the second electrodes 6 and 7 constitutes a sensor 28 for detecting both the oxygen under the high load drive mode and the temperature of the cylindrical member 1, while the first electrodes 2, 3, the lead wires 2a, 3a connected thereto, the oxygen gas diffusion limiting layer 5 and the portion of the cylindrical member between the first electrodes 2 and 3 constitutes a lean sensor 29.

In operation, when the internal combustion engine is driven, the exhaust gas from the engine enters the cover 26 through the exhaust-gas introducing openings 27.

The oxygen concentration in the exhaust gas varies with the air-fuel ratio and generally is low under the high load drive mode and under the partial load drive mode.

Let is be assumed that the air-fuel ratio is substantially equal to the stoichiometrical air-fuel ratio under the high load drive mode of the internal combustion engine. To this end, the sensor 28 of both the oxygen under the high load drive mode and the temperature of the cylindrical member 1 is used.

Since the interior of the cylindrical member 1 communicates with the atmosphere through the hole 12 in the heater 11, the atmospheric gas is within the cylindrical member 1. Further, the outer surface 1c of the cylindrical member 1 communicates with the exhaust gas through the pores of the protecting film 10. Accordingly, since the inner surface 1d of the cylindrical member 1 is exposed to the high concentration oxygen in the atmospheric gas and the outer surface 1d of the cylindrical member 1 is exposed to the oxygen in the exhaust gas, an electromotive force corresponding to the difference in oxygen concentration between the outer surface 1c and the inner surface 1d of the cylindrical member 1 is produced in the cylindrical member 1. This electromotive force (sensed electromotive force) is transmitted from the second electrodes 6, 7 to the microcomputer through the lead wires 6a, 7a, 16a and 16d.

The electromotive force corresponding to the stoichiometric air-fuel ratio for each acceleration drive or high load drive modes is previously set in the microcomputer. In the microcomputer, the sensed electromotive force is compared with the previously set electromotive force. If the sensed electromotive force is greater than the set electromotive force, it can be determined that the then sensed air-fuel ratio is smaller or lower than the stoichiometrical air-fuel ratio. Conversely, if the sensed electromotive force is smaller than the set electromotive force, it can be determined that the sensed air-fuel mixture is leaner than that the air-fuel mixture at the stoichiometrical air-fuel ratio. If there is such difference, a command from the microcomputer to decrease or increase the fuel is sent to the fuel injecting device, thereby to equalize the existing air-fuel ratio with the stoichiometrical air-fuel ratio. Harmful gases CO, HC and NOx in the exhaust gas are minimized at substantially stoichiometric air-fuel ratio. Thus, air pollution due to the exhaust gas is much decreased.

Meanwhile, when the exhaust gas from the internal combustion engine at the stoichiometrical air-fuel ratio or at the an air-fuel ratio approximate thereto is introduced into the protecting cover 26, the electromotive force in the cylindrical member 1 is sharply varied. Accordingly, by inputting this variation into the microcomputer it is also possible to easily and reliably set to the stoichiometrical air-fuel ratio. Note here that the heater 11 is caused to generate heat so as to permit the sensor 28 to be kept at a fixed minimum operating temperature of, for example, 400° C. or more.

Let it be assumed that the lean sensor 29 is used to permit the internal combustion engine to be driven under the lean or high air-fuel ratio mode.

First, the lead wire 15a and the lead wire 15b are connected to the anode and cathode of a power supply, respectively, and a current is allowed to flow through the lead wires 13a, 13b of the heater 11 thereby to cause the heater 11 to generate heat, and a voltage is applied between the lead wires 15a and 15b so as to permit the electrode 2 to have positive polarity while the electrode 3 has negative polarity. The oxygen molecules in the exhaust gas passes through the oxygen-gas diffusion limiting layer 5 and reach the electrode 3 and are given electrons to be turned into oxygen ions. Since the cylindrical member 1 is formed of oxygen-ion permeable electrolyte, the oxygen ions are diffused into the cylindrical member 1 from the electrode 3 toward the electrode 2 thus to reach the electrode 2. At this time, the oxygen ions release the electrons to cause a current (sensed current) to flow from the electrode 2 toward the electrode 3 and change to molecules which, in turn, pass through the hole 12 into the open air.

As the voltage applied between the electrodes 2 and 3 is gradually increased under a lean mode, the current between both the electrodes 2 and 3 eventually ceases to vary at some area. The current is here called "saturation current" and when the area of the electrode 3, the thickness of the oxygen-gas diffusion limiting layer 5 and the absolute temperature are set at a fixed value, the following equation holds true:

$$I = KP$$

where K is a constant and P represents the partial pressure of oxygen in the exhaust gas.

The voltage corresponding to the saturation current I is now applied between the electrodes 2 and 3. The current between the electrodes 2 and 3 with that voltage applied therebetween is here called "sensed current".

For the purpose reliably to keep the oxygen diffusion at a specified deffusion rate and precisely to sense the current between the electrodes 2 and 3, the oxygen-gas diffusion limiting layer 5 is made to have a specified thickness and the electrode 3 is made small in area. For example, the thickness is set to 200 to 800μ and the area is set to 20 mm².

The set currents (or the saturation currents) which correspond to optimum air-fuel ratios for the engine modes of lean mixture are previously set in the microcomputer. The sensed current value is supplied from the electrodes 2, 3 to the microcomputer through the lead wires 2a, 3a, 15a and 15b. Thus, in the microcomputer, the sensed current corresponding to the existing driving mode of the engine is compared with the current value previously set in the microcomputer. If the sensed current value is greater than the set current value, determination can be made in the microcomputer such that the existing air-fuel ratio is higher than the optimum air-fuel ratio, or in the reverse case such that the former is lower than the latter. In accordance with such determination, a command to decrease or increase the fuel is applied to the fuel injecting device, thus the then existing air-fuel ratio is made equal to the optimum air-fuel ratio. Thus, the fuel can be saved and the harmful gaseous components in the exhaust gas can also be decreased. When there is no difference between the current and the sensed current, it can be generally considered that an optimum air-fuel ratio has been obtained. More preferably, however, the voltage between the electrodes 2 and 3, under such conditions, is further varied and it is detected by the microcomputer that no variation occurs in the sensed current. Then, the optimum air-fuel ratio will be reliably obtained.

Meanwhile, the lean sensor 29 is required to be kept at a fixed temperature of 700° to 750° C. The lean sensor 29 is heated by the ceramic heater 11 and the temperature of the lean sensor 29 is sensed by the sensor 28 of the oxygen under a high load drive mode and the temperature of the cylindrical member 1. That is, the sensor 28 is used to sense the temperature of the cylindrical member 1 when the internal combustion engine is driven under the partial load drive mode.

As above described, the cylindrical member 1 has the negative-resistance temperature characteristic and, if a fixed voltage is kept applied between the second electrodes 6 and 7, the current between the electrodes 6 and 7 increases in proportion to a rise in the temperature of cylindrical member 1, so that the temperature is known from that current value. Accordingly, the sensed current value transmitted from the electrodes 6, 7 to the microcomputer through the lead wires 6a, 7a, 16a and 16b is compared, in the microcomputer, with the set current value corresponding to the fixed temperature set to a value between 700° and 750° C. Thus, if the temperature is below 700° C., a current is allowed to flow in the heater 11 to cause the same to generate heat, while if the temperature is 750° C., the current to the heater 11 is stopped. If the device according to the invention is used, control can be made of the air-fuel ratio of 14.5 to 25. Further, the temperature control can be made by sensing the variation in resistance of the ceramic heater 11 but in this case use is not made of the thermister characteristic of the cylindrical member 1. Therefore, the heater 11 performs both the heating function and the temperature sensing function.

It is to be noted that since the outer surface of the outer electrode 3 of the lean sensor is covered with the oxygen-gas diffusion limiting layer 5, the electrode 3 is prevented from being exfoliated from the cylindrical member wall 1 due to repetition of the cyclic operation of cooling and heating, and also prevented from being deteriorated or degraded due to the action of lead, phosphorus, oils, and the like in the exhaust gas.

What we claim is:

1. A device for sensing the oxygen concentration in an exhaust gas, comprising:

a cup-like oxygen-ion permeable cylindrical member made of solid electrolyte consisting of oxygen-ion conducting metal oxide, said cylindrical member having an inner circumferential surface communicating with the atmosphere and an outer circumferential surface communicating with the exhaust gas for producing an electromotive force corresponding to a difference between the oxygen concentrations on said inner circumferential surface and on said outer circumferential surface and having negative-resistance temperature characteristic;

a pair of first electrodes serving as a lean sensor and each comprising a thin film made of porous metal material, said first electrodes being provided on said inner circumferential surface and outer circumferential surface of said cylindrical member, respectively, in opposed relationship to each other;

an oxygen-gas diffusion limiting layer covering said lean sensing electrode on said outer circumferential surface of said cylindrical member;

a pair of second electrodes for sensing the oxygen concentration under high load drive mode and the temperature of said cylindrical member and each comprising a thin film made of porous metal material, said second electrodes being provided, respectively, on those portions of said inner and outer circumferential surfaces of said cylindrical member which are different from the portions where said first electrodes are provided in opposed relationship to each other; and a heater disposed in said cylindrical member for heating said cylindrical member.

2. The device according to claim 1, further comprising a porous electrode protecting layer covering said second electrode provided on said outer circumferential surface of said cylindrical member.

3. The device according to claim 2, wherein said porous electrode protecting layer is made of one compound selected from the group consisting of $Al_2O_3$, $Al_2O_3 \cdot MgO$ and $ZrO_2$.

4. The device according to claim 2, wherein said heater comprises a ceramic cylindrical main body having a bore formed coaxially therein, and a heating wire disposed in said main body.

5. The device according to claim 3, further comprising a housing holding said cylindrical member and having exhaust-gas introducing openings communicating with said first electrode and said second electrode which are provided on said outer circumferential surface of said cylindrical member.

6. The device according to claim 5, wherein said cylindrical member has an annular enlarged portion at a position different from that at which said electrodes are provided, and said housing has therein an annular seat portion receiving said annular enlarged portion of said cylindrical member.

7. The device according to claim 6, further comprising talc filled in a space defined between said cylindrical member and said housing and an asbestos ring covering said talc in said space.

8. The device according to claim 1, wherein said electrodes are made of platinum.

9. The device according to claim 8, wherein said cylindrical member is made of one compound selected from the group consisting of $ZrO_2$-$Y_2O_3$, $ZrO_2$-$Yb_2O_3$, $ZrO_2$-$Sc_2O_3$, $ZrO_2$-$CaO$, $ZrO_2$-$Th_2O_3$, $ZrO_2$-$MgO$, $ThO_2$-$CaO$ and $CeO_2$-$MgO$.

10. The device according to claim 9, wherein said oxygen gas diffusion limiting layer is made of one compound selected from the group consisting of $Al_2O_3$, $Al_2O_3 \cdot MgO$ and $ZrO_2$.

* * * * *